United States Patent [19]
Lüthy

[11] 4,450,157
[45] May 22, 1984

[54] THIAZOLINE DERIVATIVES

[75] Inventor: Christoph Lüthy, Schwerzenbach, Switzerland

[73] Assignee: Hoffmann-La Roche Inc., Nutley, N.J.

[21] Appl. No.: 387,305

[22] Filed: Jun. 11, 1982

[30] Foreign Application Priority Data

Jun. 19, 1981 [CH] Switzerland ............. 4072/81
Apr. 14, 1982 [CH] Switzerland ............. 2257/82

[51] Int. Cl.³ .................... A01N 57/16; C07F 9/65
[52] U.S. Cl. ........................... 424/200; 548/119
[58] Field of Search ............. 548/119, 197; 424/200

[56] References Cited
U.S. PATENT DOCUMENTS 4,339,444 7/1982 D'Silva et al. .................. 548/119

Primary Examiner—Richard Raymond
Attorney, Agent, or Firm—Jon S. Saxe; George M. Gould; John J. Maitner

[57] ABSTRACT

Heterocyclic compounds of the formula

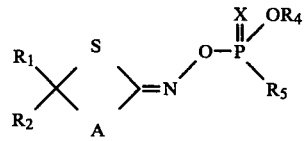

wherein A is a group

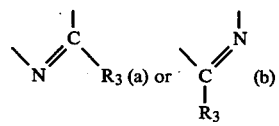

and $R_1$, $R_2$, $R_3$, $R_4$, $R_5$ and X are as defined hereinafter, process for their preparation, as well as pesticidal compositions containing one or more of these compounds as the active ingredient and methods for using the pesticidal compositions for the control of pests, particularly insects, mites and nematodes, are described.

19 Claims, No Drawings

THIAZOLINE DERIVATIVES

SUMMARY OF THE INVENTION

This invention is directed to heterocyclic compounds, particularly oxime phosphates, of the formula

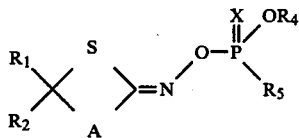

wherein
A is a group

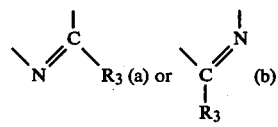

$R_1$ and $R_2$ are hydrogen, lower alkyl or cycloalkyl, or together with the carbon atom to which they are attached are a 4- to 6-membered, saturated hydrocarbon ring,
$R_3$ is lower alkyl, cycloalkyl or lower alkylthio,
X is oxygen or sulfur,
$R_4$ is lower alkyl,
$R_5$ is lower alkoxy, lower alkylthio, lower alkenylthio, lower alkynylthio, lower alkylamino or di(lower alkyl)amino, with the proviso that $R_1$, $R_2$ and $R_3$ are lower alkyl groups when A represents a group (b).

In another aspect, the invention relates to pesticidal compositions and methods of use.

DETAILED DESCRIPTION OF THE INVENTION

The present invention comprises heterocyclic compounds, particularly oxime phosphates, of the formula

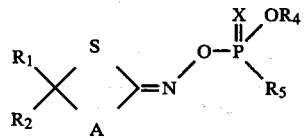

wherein
A is a group

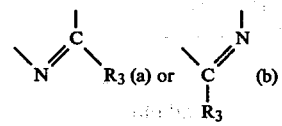

$R_1$ and $R_2$ are hydrogen, lower alkyl or cycloalkyl, or together with the carbon atom to which they are attached are a 4- to 6-membered, saturated hydrocarbon ring,
$R_3$ is lower alkyl, cycloalkyl or lower alkylthio,
X is oxygen or sulfur,
$R_4$ is lower alkyl,
$R_5$ is lower alkoxy, lower alkylthio, lower alkenylthio, lower alkynylthio, lower alkylamino or di(lower alkyl)amino, with the proviso that $R_1$, $R_2$ and $R_3$ are lower alkyl groups when A represents a group (b).

As used herein, the terms "lower alkyl", "lower alkoxy", "lower alkylthio", "lower alkenylthio", "lower alkynylthio" and "lower alkylamino" denote not only straight-chain but also branched-chain groups. The term "lower alkyl" denotes alkyl groups containing 1 to 4 carbon atoms, i.e. methyl, ethyl, n-propyl, isopropyl, n-butyl, isobutyl, sec.butyl and tert.butyl. This also applies for groups which contain lower alkyl groups, i.e. lower alkylthio, lower alkoxy, lower alkylamino and di(lower alkyl)amino. The terms "lower alkenylthio" and "lower alkynylthio" denote those groups containing 2 to 5 carbon atoms such as vinylthio, allylthio, butenylthio, pentenylthio and propargylthio. The term "cycloalkyl" includes cyclopropyl, cyclobutyl, cyclopentyl and cyclohexyl. $R_1$ and $R_2$ or the two lower alkyl groups of the di(lower alkyl)amino group can be the same or different.

Since the compounds of formula I can contain an asymmetric phosphorus atom and/or asymmetric carbon atoms, they can exist as optical antipodes. In addition, as a consequence of any double bond which is present in the compounds of formula I, geometric isomerism can occur in these compounds. Formula I is, accordingly, intended to include all of these possible isomeric forms.

If $R_1$ or $R_2$ is lower alkyl, this group is preferably methyl or ethyl. Moreover, the total number of carbon atoms in the substituents $R_1$ and $R_2$ preferably does not exceed the number 4. Where $R_1$ and $R_2$ together with the carbon atom to which they are attached denote a 4- to 6-membered, saturated hydrocarbon ring, this is preferably a cyclopentane ring.

A is preferably a group (a).
$R_1$ and $R_2$ each preferably denote hydrogen or lower alkyl, especially methyl.
$R_3$ is preferably lower alkyl, especially methyl.
X is preferably sulfur.
$R_4$ is preferably methyl or ethyl, especially ethyl.
$R_5$ is preferably lower alkylthio, especially methylthio, ethylthio, n-propylthio, isopropylthio, isobutylthio, or sec.butylthio, with n-propylthio being particularly preferred. In general, an alkyl, alkenyl or alkynyl group present in the substituent $R_5$ is preferably methyl, ethyl, n-propyl, isopropyl, isobutyl or sec.butyl; allyl; or propargyl.

Representative compounds of formula I are:
O-Ethyl-S-(sec.butyl)-(2,2,4-trimethyl-3-thiazolin-5-ylideneaminooxy)phosphonothioate,
O-ethyl-S-(n-propyl)-(2,2-dimethyl-4-cyclopropyl-3-thiazolin-5-ylideneaminooxy)phosphonodithioate,
O-ethyl-S-isobutyl-(2,2,4-trimethyl)-3-thiazolin-5-ylideneaminooxy)phosphonodithioate,
O-methyl-S-methyl-(2,2,4-trimethyl-3-thiazolin-5-ylideneaminooxy)phosphonothioate,
O-isopropyl-S-(n-propyl)-(2,2,4-trimethyl-3-thiazolin-5-ylideneaminooxy)phosphonodithioate,
O-ethyl-S-(n-propyl)-(2,2-dimethyl-4-ethylthio-3-thiazolin-5-ylideneaminooxy)phosphonodithioate,
O-ethyl-S-(n-propyl)-(2,2-dimethyl-4-tert.butyl-3-thiazolin-5-ylideneaminooxy)phosphonodithioate,
O-ethyl-S-(n-propyl)-(2,2-dimethyl-4-methylthio-3-thiazolin-5-ylideneaminooxy)phosphonothioate,
O-ethyl-S-(n-propyl)-(4,5-diethyl-5-methyl-3-thiazolin-2-ylideneaminooxy)phosphonothioate,
O-ethyl-S-(n-propyl)-(4-ethyl-5,5-dimethyl-3-thiazolin-2-ylideneaminooxy)phosphonothioate, O-ethyl-S-(sec.butyl)-(4,5-dimethyl-5-ethyl-3-thiazolin-2-ylideneaminooxy)phosphonodithioate, O-ethyl-S-allyl-(4,5-diethyl-5-methyl-3-thiazolin-2-ylideneaminooxy)phosphonodithioate and O-ethyl-S-(2-propynyl)-4,5-diethyl-5-methyl-3-thiazolin-2-ylideneaminooxy)phosphonodithioate.

Preferred compounds of formula I are:

O-Ethyl-S-(n-propyl)-(2-ethyl-2,4-dimethyl-3-thiazolin-5-ylideneaminooxy)phosphonodithioate, O-ethyl-S-(n-propyl)-(2-isopropyl-4-methyl-3-thiazolin-5-ylideneaminooxy)phosphonodithioate, O-ethyl-S-(n-propyl)-(2-cyclopropyl-2,4-dimethyl-3-thiazolin-5-ylideneaminooxy)phosphonodithioate, O-ethyl-S-(n-propyl)-(2,2-dimethyl-4-isopropyl-3-thiazolin-5-ylideneaminooxy)phosphonodithioate and O-ethyl-S-(sec.butyl)-(2,2,4-trimethyl-3-thiazolin-5-ylideneaminooxy)phosphonodithioate.

An especially preferred compound of formula I is O-ethyl-S-(n-propyl)-(2,2,4-trimethyl-3-thiazolin-5-ylideneaminooxy)phosphonodithioate.

The compounds of formula I of this invention are prepared by reacting an oxime of the formula

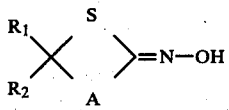

wherein A, R₁ and R₂ are as described previously, or an alkali metal, alkaline earth metal or ammonium salt thereof, optionally in the presence of an acid-binding agent, with a halide of the formula

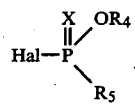

wherein

X, R₄ and R₅ are as described previously and

Hal denotes a halogen atom.

Examples of alkali metal salts or alkaline earth metal salts of the compounds of formula II which can be used in this process are the sodium, potassium, calcium and magnesium salts, preferably potassium or sodium. The halogen atom denoted by Hal in the compounds of formula III can be fluorine, chlorine, bromine or iodine, preferably chlorine.

This reaction is conveniently carried out in the presence of a solvent which is inert under the reaction conditions. Examples of an inert organic solvent which can be used in this reaction are a lower aliphatic alcohol, for example ethanol; an aliphatic ketone, for example, acetone or methyl ethyl ketone; an aliphatic ether, for example, diisopropyl ether or glycol dimethyl ether; a halogenated hydrocarbon, for example, dichloroethane or chlorobenzene; an ester, for example, ethyl acetate; an aromatic hydrocarbon, for example, benzene, toluene or a xylene; a nitrile, for example, acetonitrile; a formamide, for example, dimethylformamide; or dimethyl sulfoxide.

The reaction temperatures can be varied over a wide range, but, generally, the reaction is carried out at between room temperature and the reflux temperature of the reaction mixture, preferably between 40° C. and 90° C.

Where the starting material of formula II is not used in the form of a salt, namely an alkali metal, alkaline earth metal or ammonium salt, the reaction is conveniently carried out in the presence of an acid-binding agent. Suitable acid-binding agents include inorganic bases, for example, alkali metal or alkaline earth metal alcoholates and carbonates, and organic bases, for example, pyridine, triethylamine and the like. The alkali metal or alkaline earth metal containing bases react with the oxime of formula II with the formation of the corresponding salt which then reacts with the halide of formula III, whereupon the alkali metal or alkaline earth metal halide is liberated.

The isolation and purification of the compounds of formula I can be carried out by conventional procedures.

The product according to the foregoing process is normally obtained as a mixture of two or more isomers. The isomers can be separated using known procedures.

The oxime starting materials of formula II where A is a group (a) and R₃ is lower alkyl or cycloalkyl can be prepared by nitrosating a thiazoline of the formula

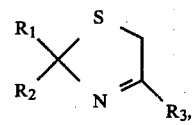

wherein

R₁ and R₂ are as described previously and

R₃ denotes lower alkyl or cycloalkyl, conveniently in the presence of a diluent.

The nitrosation is conveniently carried out according to known methods, namely using a nitrite, e.g. an alkali metal nitrite such as sodium nitrite, and an acid, e.g. acetic acid, propionic acid, a mixture of acetic acid and acetic anhydride or an aqueous mineral acid such as hydrochloric acid; nitrogen tetroxide; nitrosyl chloride; or an alkyl nitrite, e.g. methyl, ethyl or isopentyl nitrite. The latter nitrosating compounds, i.e. alkyl nitrites, can be used not only in acidic medium but also in alkaline medium.

Examples of diluents which can be employed in this reaction include water, alcohols, acetonitrile, aromatic hydrocarbons, chlorinated hydrocarbons as well as ethers.

The nitrosation reaction is conveniently carried out at a temperature between −20° C. and 100° C., preferably between 0° C. and 60° C.

The isolation and, when desired, purification of the oximes of formula II can be carried out using known procedures. For example, the diluent can be removed, for example, by filtration or distillation, and the residue can be either washed, for example, with water, dried, and crystallized or purified chromatographically, or the residue can be taken up in a suitable solvent, washed with water, the solution dried over a suitable drying agent, for example, anhydrous sodium sulfate, and, after distillation of the solvent, the product can be recrystallized or purified chromatographically.

The thiazolines of formula IV, which are used as starting materials, are either known or can be prepared according to known methods, for example, as described in F. Asinger et al., Ann. 610, 17–24 and 33–49 (1957), Angew. Chemie 79, 953 (1967) or DOS No. 2 645 731.

The starting materials of formula II wherein A is a group (a) and R₃ is lower alkylthio can conveniently be prepared according to the following Reaction Scheme:

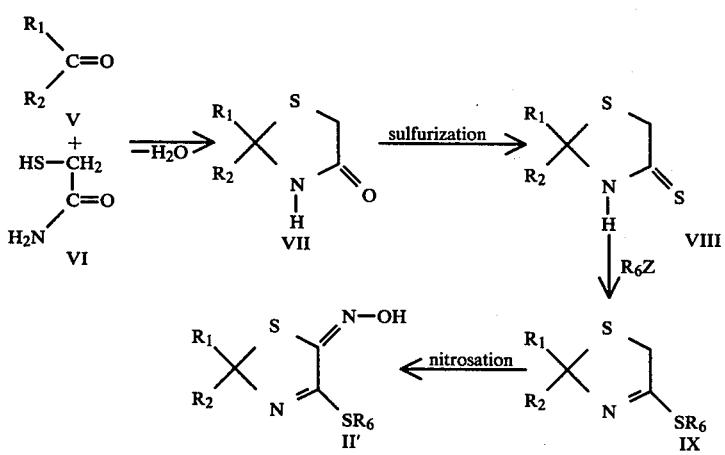

In the above Reaction Scheme R₁ and R₂ are as described previously, R₆ denotes lower alkyl and Z denotes a leaving group, for example, a halogen atom, preferably chlorine, bromine or iodine, or a mesylate or tosylate group.

The reaction of the compounds of formulae V and VI with one another is conveniently carried out in a diluent for the azeotropic removal of the water which is formed in the reaction. The reaction is also conveniently carried out in the presence of a catalytic amount of an organic acid, such as p-toluenesulfonic acid, or an inorganic acid, such as phosphorus oxychloride, or a Lewis acid, for example, zinc chloride. Examples of diluents which can be employed in this reaction include aromatics, especially benzene. The reaction is preferably carried out at the reflux temperature of the particular reaction mixture. A small excess of the compound of formula V is preferably used.

The compounds of formula V, which are used as starting materials in this reaction step, are either known or can be prepared according to known methods. The starting material of formula VI is the known 2-mercaptoacetamie (thioglycolamide) which is described, for example, in H. Sokol and J. J. Ritter, JACS 70, 3517-3518 (1948).

The 4-oxo-3-thiazoline of formula VII is converted into the corresponding 4-thio-3-thiazoline of formula VIII by direct sulfurization. For this purpose there can be used sulfurization agents such as phosphorus pentasulfide, alone or in the presence of pyridine, the phosphorus pentasulfide-pyridine (1:2) complex and the dimer of p-methoxy-phenylthiophosphine sulfide [see, for example, S. -O. Lawesson et al., Bull. Soc. Chim. Belg. 87, 229-238 (1978)]. An inert organic diluent such as an aromatic solvent, for example, toluene, xylene or pyridine, or hexamethylphosphoric acid triamide is advantageously used. The reaction can be carried out at a temperature between room temperature and the reflux temperature of the reaction mixture, preferably between 80° C. and 140° C.

The alkylation of a compound of formula VIII with an alkylating agent of the formula R₆Z is conveniently carried out in a polar inert organic solvent such as a lower aliphatic alcohol, for example, ethanol; an ether or an ether-like compound, for example, tetrahydrofuran; a nitrile, for example, acetonitrile; or a formamide, for example, dimethylformamide. Moreover, the reaction is preferably carried out in the presence of a base or an acid-binding agent, as such sodium hydride, sodium hydroxide, potassium carbonate, pyridine, triethylamine, and the like. The reaction is conveniently carried out at a temperature between 0° C. and the reflux temperature of the reaction mixture. The lower alkyl bromides and iodides have been found to be especially suitable alkylating agents of formula R₆Z.

The last step of this route to the intermediates of formula II' comprises nitration of a 4-alkylthio-3-thiazoline of formula IX. The nitrosation is conveniently carried out analogously to the process described above in connection with the nitrosation of the thiazoline of formula IV.

The isolation and, when desired, purification of the product of any reaction step can be carried out by conventional procedures.

The remaining starting materials of formula II, i.e. those in which A denotes a group (b) and R₁, R₂ and R₃ each denote lower alkyl, can be prepared in a simple manner by reacting an α-thiocyanato ketone of the formula

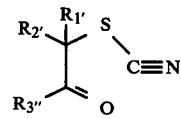

wherein $R_{1'}$, $R_{2'}$ and $R_{3''}$ denote lower alkyl,
with hydroxylamine in the presence of a solvent, preferably an alcohol or an aqueous alcohol. The reaction is conveniently carried out at temperatures between 5° C. and 100° C., preferably between 25° C. and 40° C. The hydroxylamine is preferably used in the form of an acid addition salt, especially the hydrochloride, in the presence of an acid-binding agent such as, for example, sodium bicarbonate or sodium acetate. Isolation of the compounds of formula II can be carried out, for example, by digesting with water the solid resulting during the reaction after distillation of the solvent, filtering-off the solid, drying the solid, and optionally recrystallizing. Alternatively, the solid can be dissolved in a suitable solvent, washed with water, dried over a suitable drying agent, for example, anhydrous sodium sulfate, and, after distilling off of the solvent, recrystallizing or purifying by chromatography.

Some of the α-thiocyanato ketones of formula X, which are used as starting materials, are known and can be prepared according to known processes, for example by replacing the halogen atom in α-halo ketones by the thiocyanato group using metal rhodanides in a suitable solvent such as acetone or dimethylformamide. Some of the required α-halo ketones are known and can be prepared according to known processes such as, for example, by halogenating the carbonyl compounds with bromine or dioxan or N-bromosuccinimide in carbon tetrachloride.

The halides of formula III, which are used as starting materials, are either known or can be prepared according to known methods, for example, as described in Houben-Weyl, Methoden der Organischen Chemie, Volume XII/2 (1964), p. 274–276, 283–291, 293–298, 405–410, 607–610, 613–622, 689, and 755–758, British Patent Specification No. 1 552 658, German Auslegeschriften Nos. 2 532 396 and 2 642 982 and German Offenlegungsschriften Nos. 2 804 775 and 2 804 796.

The compounds of formula I of this invention are active as pesticides and most valuable in the control of insects, mites and nematodes. They are especially valuable against:

Coleoptera such as, for example, Epilachna spp., *Leptinotarsa decemlineata*, Anthonomus spp., *Conotrachelus nenuphar*, Lema spp., *Lissorhoptrus oryzaephilus*, Phyllotreta spp., *Psylliodes chrysocephala, Meligethes aenus, Ceutorrhynchus assimilis*, Agriotes spp., *Otiorhynchus sulcatus, Melolontha melolontha* and Diabrotica spp.

Lepidoptera such as, for example, Laspeyresia spp., *Adoxophyes orana, Tortrix viridana, Cheimatobia brumata, Lyonetia clerkella, Operophtera brumata, Lithocolletis blancardella, Porthetria diapar, Mamestra brassicae, Agrotis segetum*, Plutella spp., *Pieris brassicae, Choristoneura fumiferana*, Heliothis spp., Spodoptera spp., *Pectinophora gossipiella*, Chilo spp., *Ostrinia nubilalis, Clysia ambiguella, Lobesia botrana*.

Diptera such as, for example, *Drosophila melanogaster*, Ceratitis spp., *Oscinella frit*, Dacus spp. and Rhagoletis spp. leatherjacket spp., Sciara spp., Phorbia spp. and *Megasetia agarici*.

Homoptera, i.e. aphids such as, for example, *Aphis fabae, Myzus persicae* and other species of these genera, Rhophalosiphon spp., Schizaphis spp., Dysaphis spp., Eriosoma spp., Macrosiphum spp., Adelges spp., *Sitobion avenae*, Metopolophium spp. as well as *shield* and *soft* lice such as, for example, Aspidiotus spp., Saissetia spp., *Quadraspidiotus perniciosus, Aonidiella aurantii*, Coccus spp., Lepidosaphes spp., Planococcus spp., Pseudococcus spp., Ceroplastes spp., *Icerya purchasi*, Chrysomphalus spp., Parlatoria spp., Rhizoecus spp. as well as cicada such as, for example, Nephotettix spp., Laodelphax spp., Nilaparvata spp., Sogatella spp. and Erythroneura spp., Aleurodidae such as, for example, *Trialeurodes vaporariorum*, Dialeurodes spp., Aleurothrixus spp., Bemisia spp., Aleyrodes spp., moreover thrips species and bugs. Acarina such as, for example, *Tetranychus urticae, Panonychus ulmi* and other Tetranychida, Tarsonemida such as neotarsenemus spp., Tenuipalpidae such as Brevipalpus, Eriophyida such as *Phyllocoptruta oleivora, Aceria sheldoni*, Eriophyes spp., Aceria spp. and ticks.

Nematoda such as, for example, free-living nematodes (inter alia Pratylenchus spp. such as *P. penetrans*), leaf-parasitic nematodes (inter alia Aphelenchoides) and root-parasitic nematodes (inter alia Meloidogynae spp. such as M. incognita, Globodera spp. such as *G. rostochiensis*).

The compounds of formula I of this invention are active as contact and feed poisons. In addition, some of the compounds are taken up in plants, so that the pests to be controlled are exterminated upon eating the plants.

The instant invention is also directed to pesticidal compositions such as solutions, emulsions, suspensions, foams, powders, pastes and granulates which contain inert carrier materials and, as the active ingredient, one or more of the compounds of formula I.

These compositions are prepared by known methods, such as, for example, by mixing the active substance with extenders (liquid solvents, liquified gases under pressure and/or solid carrier substances) and, if desired, surface-active agents (emulsifiers, wetting agents or dispersing agents). When water is used as the extender, organic solvents can also be used as auxiliary solvents.

Examples of liquid solvents include: aromatics, such as toluene, xylenes and alkylnaphthalenes; chlorinated aromatics and chlorinated aliphatic hydrocarbons, such as chlorobenzenes, chloroethylenes and methylene chloride; aliphatic hydrocarbons, such as cyclohexane and paraffins (e.g., petroleum fractions); alcohols, such as butanol and glycol as well as their ethers and esters; ketones, such as acetone, methyl ethyl ketone, methyl isobutyl ketone, and cyclohexanone; strongly polar solvents, such as dimethylformamide, N-methylpyrrolidone and dimethylsulfoxide, and water.

By liquified gaseous extenders or carrier substances are meant liquids which are gaseous at normal temperature and under normal pressure, such as aerosol propellants, e.g. halogenated hydrocarbons (e.g. dichlorodifluoromethane).

Examples of solid carrier substances include natural mineral substances, such as kaolins, clays, talc, chalk, quartz, attapulgite, montmorillonite and diatomaceous earth, and synthetic mineral substances, such as high-dispersible silicic acid, aluminum oxide and silicates.

Surface-active agents, especially emulsifying agents and wetting agents, suitable for use in the pesticidal compositions of this invention can be non-ionic or anionic. Examples of non-ionic emulsifiers which can be used include polyoxyethylene-fatty acid esters, polyoxyethylene-fatty alcohol ethers and alkylaryl-polyglycol ethers. Examples of anionic emulsifiers include alkyl sulfonates, alkyl sulfates and aryl sulfonates.

Examples of dispersing agents include lignin, sulfite lyes and methyl cellulose.

The pesticidal compositions of this invention generally contain between 0.0005 percent by weight and 95 percent by weight of compound or compounds of formula I as active ingredient, preferably between 1 percent by weight and 75 percent by weight.

The pesticidal compositions of the present invention can be in forms suitable for storage or shipment. In such forms (e.g., emulsifiable concentrates), the concentration of active ingredients is normally at the higher end of the above concentration range. These forms can then be diluted with the same or different carrier materials to afford active ingredient concentrations suitable for practical use, and such concentrations normally lie at the lower end of the above-noted concentration range.

The application forms prepared from the above-indicated forms include ready-for-use solutions, emulsions, foams, suspensions, powders, pastes, soluble powders, dusting agents and granulates. They are applied by conventional procedures, such as sprinkling, spraying, smokescreening, dusting, scattering, drilling-in, vaporizing, pouring, drenching or incrustating.

The concentrations of active ingredient in the ready-for-use preparations can vary over wide limits. In spray liquors, the concentration can be, for example, between 0.0005 percent by weight and 20 percent by weight.

The active ingredients can also be used with good effect in the ultra-low-volume process (ULV) where it is possible to formulate spray liquors having preferably from about 10 to about 20 percent by weight.

The active ingredients can also be used with good effect in the low-volume process and in the high-volume process where it is possible to formulate spray liquors having from 0.5 to 1.0 and 0.05 to 0.1 percent by weight of active ingredient respectively.

In granulates, the concentration of active ingredients is preferably from about 2 to about 10 percent by weight of the compound or compounds of formula I as the active substance.

The pesticidal compositions of the present invention can contain other active substances, for examples, other pesticides, besides the compounds of formula I. Such combination compositions are suitable for increasing the activity or for broadening the spectrum of activity.

In preparing the pesticidal compositions of the present invention, the active ingredient of formula I is mixed with inert carrier material. In the case of pulverous compositions, the active ingredient can be mixed with the solid carrier material, for example, by milling together, or the inert carrier material can be impregnated with a solution or suspension of the active ingredient and then the solvent or suspension agent can be removed by evaporation, heating or by filtering under reduced pressure. By the addition of wetting and/or dispersing agents, such pulverous compositions can be made readily wettable with water so that they can be converted into aqueous suspensions which are suitable, for example, as spray compositions. For the preparation of emulsifiable concentrates, which are especially suitable for storage and shipment, the active ingredient can be mixed, for example, with an emulsifying agent or dissolved in an inert solvent and thereafter mixed with an emulsifier. Ready-for-use emulsions are prepared by diluting such concentrates with water.

The pesticides of the present invention are used by treating the locus to be protected or the pests themselves with a compound of this invention or with the pesticidal compositions of the present invention. This method of use is preferably carried out by applying the composition to the soil or leaves, or by application to provisions or materials to be protected, depending on the pests to be controlled.

The following Examples illustrate the invention.

EXAMPLE 1

15.8 g (0.1 mol) of 5-oxo-2,2,4-trimethyl-3-thiazoline oxime and 83 g (0.6 mol) of anhydrous potassium carbonate are suspended in 300 ml of absolute acetonitrile and treated with 25.7 g of 85% O-ethyl-S-(n-propyl)-dithiophosphoric acid ester chloride (0.1 mol). The mixture is stirred well at 50° C. The solid consisting mainly of potassium salts is subsequently filtered off and the acetonitrile is removed from the solution by evaporation. The residue is purified by dissolving it in toluene, washing it neutral with 5 percent sodium bicarbonate solution and then with semi-saturated sodium chloride solution, drying over anhydrous sodium sulfate and removing the solvent under reduced pressure. The oily crude product is heated to 75° C. in a high vacuum to constant weight to yield O-ethyl-S-(n-propyl)-(2,2,4-trimethyl-3-thiazolin-5-ylideneaminooxy)-phosphonodithioate as a light brown oil; $n_D^{20} = 1.5583$.

This product is further purified by filtering it on silica gel to yield an analytically pure, almost colorless oil; $n_D^{22} = 1.5590$.

EXAMPLE 2–23

The corresponding starting materials of formula II and III are reacted analogously to the process described in Example 1 to give the compounds of formula I listed in Table 1 hereinafter.

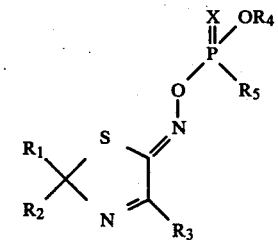

TABLE 1

| Example | R$_1$ | R$_2$ | R$_3$ | X | R$_4$ | R$_5$ | n$_D$/m.p. |
|---|---|---|---|---|---|---|---|
| 2 | CH$_3$ | CH$_3$ | CH$_3$ | S | C$_2$H$_5$ | OC$_2$H$_5$ | $n_D^{20}$ 1.5264 |
| 3 | CH$_3$ | CH$_3$ | CH$_3$ | S | CH$_3$ | OCH$_3$ | $n_D^{20}$ 1.5420 |
| 4 | CH$_3$ | CH$_3$ | CH$_3$ | O | C$_2$H$_5$ | SC$_3$H$_7$-n | $n_D^{20}$ 1.5280 |
| 5 | CH$_3$ | CH$_3$ | CH$_3$ | S | C$_2$H$_5$ | NHCH(CH$_3$)$_2$ | m.p. 91° C. |
| 6 | C$_2$H$_5$ | CH$_3$ | CH$_3$ | S | C$_2$H$_5$ | SC$_3$H$_7$-n | $n_D^{20}$ 1.5571 |
| 7 | C$_2$H$_5$ | n-C$_4$H$_9$ | CH$_3$ | S | C$_2$H$_5$ | SC$_3$H$_7$-n | $n_D^{20}$ 1.5465 |
| 8 | isoC$_3$H$_7$ | H | CH$_3$ | S | C$_2$H$_5$ | SC$_3$H$_7$-n | $n_D^{20}$ 1.5592 |
| 9 | ▷ | CH$_3$ | CH$_3$ | S | C$_2$H$_5$ | SC$_3$H$_7$-n | $n_D^{20}$ 1.5602 |
| 10 | —(CH$_2$)$_4$— | | CH$_3$ | S | C$_2$H$_5$ | SC$_3$H$_7$-n | $n_D^{20}$ 1.5742 |
| 11 | CH$_3$ | CH$_3$ | isoC$_3$H$_7$ | S | C$_2$H$_5$ | SC$_3$H$_7$-n | $n_D^{20}$ 1.5460 |
| 12 | CH$_3$ | CH$_3$ | isoC$_3$H$_7$ | O | C$_2$H$_5$ | SC$_3$H$_7$-n | $n_D^{20}$ 1.5185 |
| 13 | CH$_3$ | CH$_3$ | SCH$_3$ | S | C$_2$H$_5$ | SC$_3$H$_7$-n | $n_D^{20}$ 1.5773 |
| 14 | CH$_3$ | CH$_3$ | CH$_3$ | s | C$_2$H$_5$ | S sec.C$_4$H$_9$ | $n_D^{23}$ 1.5532 |
| 15 | CH$_3$ | CH$_3$ | CH$_3$ | S | C$_2$H$_5$ | SCH$_2$C≡CH | m.p. 56–58° C. |
| 16 | CH$_3$ | CH$_3$ | CH$_3$ | S | C$_2$H$_5$ | SCH$_2$CH=CH$_2$ | $n_D^{23}$ 1.5708 |

TABLE 1-continued

| Example | R₁ | R₂ | R₃ | X | R₄ | R₅ | $n_D$/m.p. |
|---|---|---|---|---|---|---|---|
| 17 | CH₃ | CH₃ | CH₃ | S | C₂H₅ | SC₂H₅ | $n_D^{20}$ 1.5640 |
| 18 | CH₃ | CH₃ | CH₃ | O | C₂H₅ | OC₂H₅ | $n_D^{20}$ 1.4972 |
| 20 | CH₃ |  | CH₃ | O | C₂H₅ | SC₃H₇-n | $n_D^{20}$ 1.5368 |
| 20 | H | isoC₃H₇ | CH₃ | O | C₂H₅ | SC₃H₇-n | $n_D^{20}$ 1.5292 |
| 21 | CH₃ | C₂H₅ | CH₃ | O | C₂H₅ | SC₃H₇-n | $n_D^{20}$ 1.5180 |
| 22 | H | CH₃ | CH₃ | S | C₂H₅ | SC₃H₇-n | $n_D^{20}$ 1.5696 |
| 23 | H | CH₃ | CH₃ | O | C₂H₅ | SC₃H₇-n | $n_D^{20}$ 1.5360 |

EXAMPLE 24

2.5 g (0.0145 mol) of 2-oxo-4,5-dimethyl-5-ethyl-3-thiazoline oxime, 4.0 g (0.029 mol) of anhydrous potassium carbonate and 2.0 g of anhydrous sodium sulfate are suspended in 20 ml of acetonitrile. 3.08 g (0.0152 mol) of O-ethyl-S-(n-propyl)-thiophosphoric acid ester chloride are added dropwise at 55° C. The mixture is stirred at this temperature for 40 minutes, cooled to room temperature and subsequently filtered through Celite in order to remove resulting salts. The acetonitrile is removed from the solution by evaporation under reduced pressure. The residue is purified by dissolving it in toluene, washing the solution twice with water, drying over anhydrous sodium sulfate and removing the solvent under reduced pressure. The oily product is dissolved in chloroform, filtered on silica gel and finally evaporated to yield O-ethyl-S-(n-propyl)-(4,5-dimethyl-5-ethyl-3-thiazolin-2-ylideneaminooxy)phosphonothioate as a colorless oil; $n_D^{26.5}$ = 1.5341.

EXAMPLES 25-34

The corresponding starting materials of formula II and III are reacted analogously to the process described in Example 24 to give the compounds of formula I listed in Table 2 hereinafter.

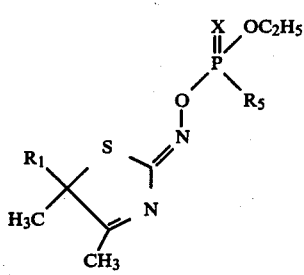

TABLE 2

| Example | R₁ | X | R₅ | $n_D$/m.p. |
|---|---|---|---|---|
| 25 | CH₃ | S | OC₂H₅ | $n_D^{20}$ 1.5461 |
| 26 | CH₃ | S | SC₃H₇-n | $n_D^{20}$ 1.5738 |
| 27 | CH₃ | O | SC₃H₇-n | $n_D^{20}$ 1.5372 |
| 28 | C₂H₅ | S | SC₃H₇-n | $n_D^{20}$ 1.5710 |
| 29 | CH₃ | O | OC₂H₅ | $n_D^{20}$ 1.5009 |
| 30 | CH₃ | S | N(CH₃)₂ | m.p. 95° C. |
| 31 | CH₃ | S | S sec.C₄H₉ | $n_D^{20}$ 1.5671 |
| 32 | CH₃ | S | SCH₂CH=CH₂ | $n_D^{23}$ 1.5853 |
| 33 | C₂H₅ | S | OC₂H₅ | $n_D^{20}$ 1.5372 |
| 34 | C₂H₅ | O | OC₂H₅ | $N_D^{20}$ 1.5075 |

EXAMPLE 35

The 5-oxo-2,2,4-trimethyl-3-thiazoline oxime required as the starting material in Examples 1-5 and 14-18 can be prepared as follows:

7.0 g (0.1 mol) of solid sodium nitrite are added portionwise while stirring well to a mixture of 12.9 g (0.1 mol) of 2,2,4-trimethyl-3-thiazoline, 12.0 g (0.2 mol) of acetic acid, 10.2 g (0.1 mol) of acetic anhydride and 35 g of toluene at 10° C. The temperature of the mixture is allowed to rise to room temperature over 2 hours and the mixture is stirred at this temperature for an additional 16 hours. An ice-cold solution of 16 g (0.4 mol) of sodium hydroxide in 120 ml of water is then added dropwise to the mixture, a pH of about 11 being attained. The water insoluble portion is separated with 50 ml of diethyl ether. The aqueous phase is subsequently neutralized with concentrated hydrochloric acid. Almost colorless crystals precipitate when the mixture has a pH of about 6. The mixture is filtered and the crystals are washed with water and then dried at 40° C. under reduced pressure to yield 5-oxo-2,2,4-trimethyl-3-thiazoline oxime; m.p. 161°-162° C.

The 5-oxo-2,2,4-trimethyl-3-thiazoline oxime can also be prepared, for example, using those reaction conditions which are described in Examples 33 and 34 of European Patent Publication No 39 520.

EXAMPLE 36

The 5-oxo-2,2,4-trimethyl-3-thiazoline oxime can also be prepared as follows:

12.9 g (0.1 mol) of 2,2,4-trimethyl-3-thiazoline are added to a suspension of 11.2 g (0.1 mol) of potassium tertiary butoxide in 70 ml of toluene and the mixture is heated to 80° C. under nitrogen. At this temperature 11.7 g (0.1 mol) of isopentyl nitrite are then added dropwise to the well-stirred solution of the thiazoline and potassium tertiary butoxide in toluene, the temperature of the solution being maintained at 80°-90° C. without further heating. After completion of the addition, the solution is stirred for an additional 1 hour at 80° C. The solution is treated with 150 ml of water, a pH of about 9 being attained, and the resulting aqueous solution is brought into the strongly alkaline range (pH about 11) by the addition of 30% aqueous sodium hydroxide solution. The solution is extracted with 100 ml of diethyl ether and the separated aqueous phase is neutralized to about pH 7 with concentrated hydrochloric acid, to precipitate crystals of 5-oxo-2,2,4-trimethyl-3-thiazoline oxime. The crystals are filtered off, washed with water and dried at 40° C. under reduced pressure to yield a product having a melting point of 158°-160° C.

EXAMPLES 37–43

The corresponding substituted 3-thiazolines are reacted with sodium nitrate or isopentyl nitrite analogously to the process described in Example 35 or 36 to give the starting material of formula II listed in Table 3. The corresponding products of formula I are also listed in this Table.

TABLE 3

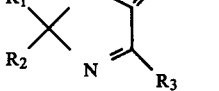

| Example | $R_1$ | $R_2$ | $R_3$ | m.p. | Example No. of the product of formula I |
|---|---|---|---|---|---|
| 37 | $C_2H_5$ | $CH_3$ | $CH_3$ | 101–102° C. | 6, 21 |
| 38 | $C_2H_5$ | $n-C_4H_9$ | $CH_3$ | — (oil) | 7 |
| 39 | $isoC_3H_7$ | H | $CH_3$ | 112° C. | 8, 20 |
| 40 |  | $CH_3$ | $CH_3$ | 98° c. | 9, 19 |
| 41 | —$(CH_2)_4$— | | $CH_3$ | 157–159° C. | 10 |
| 42 | $CH_3$ | $CH_3$ | $isoC_3H_7$ | 187–192° C. | 11, 12 |
| 43 | H | $CH_3$ | $CH_3$ | 152–154° C. | 22, 23 |

EXAMPLE 44

The 5-oxo-2,2-dimethyl-4-methylthio-3-thiazoline oxime required as the starting material in Example 13 can be prepared as follows:

60 g (0.66 mol) of 2-mercaptoacetamide, 150 ml (2.0 mol) of acetone and a catalytic amount (about 100 mg) of p-toluenesulfonic acid are dissolved in 500 ml of benzene. With the use of a water separator, the solution is heated for 72 hours to remove the water resulting in the reaction as well as about 300 ml of solvent. 100 ml (1.4 mol) of acetone and 200 ml of benzene are added and the solution is heated on the water separator for an additional 36 hours. After distillation of the solvent has been completed, the mixture is dissolved in methylene chloride. The methylene chloride solution is washed with dilute sodium bicarbonate solution and with water, and dried over anhydrous sodium sulfate. Upon concentration of the solution under reduced pressure a crystalline product, 2,2-dimethyl-4-thiazolidinone, m.p. 125°–127° C., precipitates.

14.4 g (0.11 mol) of 2,2-dimethyl-4-thiazolidinone, 8.2 g (0.037 mol) of phosphorus pentasulphide and 3 ml (0.037 mol) of pyridine in 75 ml in xylene are heated at reflux under nitrogen for 5 hours. The mixture is then poured into ice/water and extracted twice with ethyl acetate. The organic extracts are extracted once with dilute hydrochloric acid solution and once with dilute sodium hydroxide and subsequently washed neutral with saturated sodium chloride solution. The organic solution is dried over anhydrous sodium sulfate and the solvent is evaporated. The residue is treated with activated carbon and then crystallized from ethyl acetate/n-hexane to yield 2,2-dimethyl-thiazolidine-4-thione, m.p. 106°–108° C.

6.0 g (0.041 mol) of 2,2-dimethyl-thiazolidine-4-thione are added cautiously to a suspension of 1.0 g (0.041 mol) of oil-free sodium hydride in 20 ml of absolute dimethylformamide. After completion of the evolution of hydrogen, the mixture is heated briefly to 50° C., then cooled to 0° C. and 2.6 ml (0.042 mol) of methyl iodide are added dropwise thereto. After removing the ice-bath the mixture is stirred for an additional 3 hours, treated with water and extracted twice with methylene chloride. The organic extracts are subsequently combined, washed three times with 100 ml of water each time, dried over anhydrous sodium sulfate and evaporated at 40° C. under reduced pressure to yield crude 2,2-dimethyl-4-methylthio-3-thiazoline.

6.4 g (0.04 mol) of crude 2,2-dimethyl-4-methylthio-3-thiazoline are dissolved in 40 ml of water and the solution is treated with 3.6 g (0.052 mol) of sodium nitrite and subsequently treated dropwise at 10° C. with 6.1 ml (0.11 mol) of acetic acid. After stirring the mixture for 3 hours, 3.6 g of sodium nitrite and 6.1 ml of acetic acid are added thereto and the mixture is allowed to stir for an additional 16 hours. The mixture is then diluted with water and the precipitated crystals are filtered off, to yield 5-oxo-2,2-dimethyl-4-methylthio-3-thiazoline oxime, m.p. 168°–171° C.

EXAMPLE 45

The 2-oxo-4,5,5-trimethyl-3-thiazoline oxime required as the starting material in Examples 25 to 27 and 29 to 32 can be prepared as follows:

16.5 g (0.1 mol) of 3-bromo-3-methyl-2-butanone and 11.6 g (0.12 mol) of potassium rhodanide in 150 ml of anhydrous acetone are heated at reflux for about 1½ hours. After cooling, the separated potassium bromide is filtered off under suction and backwashed with a small amount of acetone, and the filtrate is evaporated to dryness at 50° C. under reduced pressure. The residue is dissolved in 200 ml of diethyl ether and the solution is washed three times with 100 ml of water each time, dried over anhydrous sodium sulfate and evaporated to dryness under reduced pressure. The crude product is fractionated on a short Vigreux column to yield 3-methyl-3-thiocyanato-2-butanone, b.p. 52° C./0.04 mmHg.

8.3 g (0.12 mol) of hydroxylamine hydrochloride are dissolved in 50 ml of water and treated with 10.1 g (0.12 mol) of sodium bicarbonate. This solution (pH 6–7) is added at room temperature while stirring to a solution of 14.3 g (0.1 mol) of 3-methyl-3-thiocyanato-2-butanone in 100 ml of ethanol. The temperature of the mixture rises rapidly to 37° C. The mixture is subsequently stirred for an additional 1 hour and 120 ml of the solvent are distilled off at 50° C. under reduced pressure. The residue is extracted three times with 100 ml of diethyl ether each time and the organic phase is washed with a small amount of water, dried over anhydrous sodium sulfate and concentrated until crystallization begins. After cooling, the crystal slurry is treated with 10 ml of n-hexane. The crystals are filtered off under suction, washed with diethyl ether/n-hexane (2:1) and dried to yield 2-oxo-4,5,5-trimethyl-3-thiazoline oxime, m.p. 151°–153° C.

EXAMPLE 46

Analogously to the process described in Example 45, 3-bromo-3-methyl-2-pentanone and potassium rhodamide are reacted to give 3-methyl-3-thiocyanato-2-pentanone and this is then reacted with hydroxylamine hydrochloride to yield 2-oxo-4,5-dimethyl-5-ethyl-3- thiazoline oxime. The last-named compound is required as the starting material in Examples 24, 28, 33 and 34.

EXAMPLE 47

The O-ethyl-S-(2-propenyl)-dithiophosphoric acid ester chloride used as the reagent in Examples 16 and 32 can be prepared as follows:

120 g (0.53 mol) of O,O-diethyl-S-(2-propenyl)-dithiophosphoric acid triester and 270 ml of 40% aqueous dimethylamine solution (2.1 mol of dimethylamine) are stirred at 40° C. for 16 hours. 60 ml of toluene are then added thereto, the mixture is extracted and the organic phase is separated. The aqueous phase is evaporated under reduced pressure and the residue is dried at 40° C. in a high vacuum to yield O-ethyl-S-(2-propenyl)-dithiophosphoric acid dimethylammonium salt as a yellowish oil; $n_D^{23} = 1.5362$.

95 g (0.39 mol) of the aformentioned salt are added dropwise during about 1½ hours to a stirred mixture, cooled to 0° C., of 83 g (0.40 mol) of phosphorus pentachloride and 73 ml (0.80 mol) of phosphorus oxychloride and the mixture is stirred at room temperature for an additional 2 hours. The mixture is diluted with 1 liter of methylene chloride and treated with 2 liters of ice-/water. The mixture is allowed to stir at 0°–5° C. for 1 hour in order to destroy the excess reagents, the organic phase is then separated and the solvent is distilled off. The residue is distilled in a high vacuum to yield O-ethyl-S-(2-propenyl)-dithiophosphoric acid ester chloride as a colorless liquid; b.p. 46° C./0.015 mmHg.

EXAMPLE 48

Analogously to the process described in Example 47, O-ethyl-S-(2-propynyl)-dithiophosphoric acid ester chloride; b.p. 46°–48° C./0.01 mmHg is obtained from O,O-diethyl-S-(2-propynyl)-dithiophosphoric acid triester. This compound is required as the reagent in Example 15.

EXAMPLE 49

This Example illustrates a typical pesticidal composition.

The following ingredients are admixed to prepare an emulsifiable concentrate.

| Ingredient | Amount g/liter |
|---|---|
| Active substance of formula I | 500 |
| Emulsifier mixture consisting of: | 50 |
| calcium alkylaryl sulfonate, alkylphenol ethoxylate, block polymerisate of propylene oxide and ethylene oxide | |
| Calcium dodecylbenzenesulfonate | 25 |
| Solvent [mixture of mono,di- and tri (lower alkyl) benzenes] | ad 1000 ml |

I claim:

1. A compound of the formula

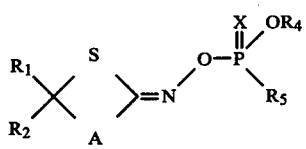

I wherein
A is a group

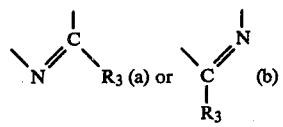

$R_1$ and $R_2$ are hydrogen, lower alkyl or cycloalkyl, or together with the carbon atom to which they are attached area 4- to 6-membered, saturated hydrocarbon ring, $R_3$ is lower alkyl, cycloalkyl or lower alkylthio, X is oxygen or sulfur, $R_4$ is lower alkyl, $R_5$ is lower alkoxy, lower alkylthio, lower alkenylthio, lower alkynylthio, lower alkylamino or di (lower alkyl) amino, with the proviso that $R_1$, $R_2$ and $R_3$ are lower alkyl groups when A represents a group (b).

2. The compound according to claim 1, wherein A is a group (a).

3. The compound according to claim 1 or claim 2, wherein $R_1$ is methyl.

4. The compound according to claim 3, wherein $R_2$ is methyl.

5. The compound according to claim 4, wherein $R_3$ is methyl.

6. The compound according to claim 5, wherein X is sulphur.

7. The compound according to claim 6, wherein $R_4$ is ethyl.

8. The compound according to claim 7, wherein $R_5$ is n-propylthio.

9. O-Ethyl-S-(n-propyl)-(2,2,4-trimethyl-3-thiazolin-5-ylidineaminooxy)-phosphonodithioate.

10. A compound according to claim 1, selected from the group consisting of:
O,O-Diethyl-(2,2,4-trimethyl-3-thiazolin-5-ylideneaminooxy)phosphonothioate,
O,O-dimethyl-(2,2,4-trimethyl-3-thiazolin-5-ylideneaminooxy)phosphonothioate,
O-ethyl-S-(n-propyl)-(2,2,4-trimethyl-3-thiazolin-5-ylideneaminooxy)phosphonothioate,
O-ethyl-(2,2,4-trimethyl-3-thiazolin-5-ylideneaminooxy)phosphonothioate isopropylamide,
O-ethyl-S-(n-propyl)-(2-ethyl-2,4-dimethyl-3-thiazolin-5-ylideneaminooxy)phosphonodithioate,
O-ethyl-S-(n-propyl)-[2-ethyl-2-(n-butyl)-4-methyl-3-thiazolin-5-ylideneaminooxy]phosphonodithioate,
O-ethyl-S-(n-propyl)-(2-isopropyl-4-methyl-3-thiazolin-5-ylideneaminooxy)phosphonodithioate,
O-ethyl-S-(n-propyl)-(2-cyclopropyl-2,4-dimethyl-3-thiazolin-5-ylideneaminooxy)phosphonodithioate,
O-ethyl-S-(n-propyl)-(2,2-tetramethylene-4-methyl-3-thiazolin-5-ylideneaminooxy)phosphonodithioate,
O-ethyl-S-(n-propyl)-(2,2-dimethyl-4-isopropyl-3-thiazolin-5-ylideneaminooxy)phosphonodithioate,
O-ethyl-S-(n-propyl)-(2,2-dimethyl-4-isopropyl-3-thiazolin-5-ylideneaminooxy)phosphonothioate,
O-ethyl-S-(n-propyl)-(2,2-dimethyl-4-methylthio-3-thiazolin-5-ylideneaminooxy)phosphonodithioate,
O-ethyl-S-(sec.butyl)-(2,2,4-trimethyl-3-thiazolin-5-ylideneaminooxy)phosphonodithioate,
O-ethyl-S-(n-propyl)-(4,5-dimethyl-5-ethyl-3-thiazolin-2-ylideneaminooxy)phosphonothioate,
O,O-diethyl-(4,4,5-trimethyl-3-thiazolin-2-ylideneaminooxy)phosphonothioate, O-ethyl-S-(n-propyl)-(4,5,5-trimethyl-3-thiazolin-2-ylideneaminooxy)phosphonodithioate,
O-ethyl-S-(n-propyl)-(4,5,5-trimethyl-3-thiazolin-2-ylideneaminooxy)phosphonothioate and
O-ethyl-S-(n-propyl)-(4,5-dimethyl-5-ethyl-3-thiazolin-2-ylideneaminooxy)phosphonodithioate.

11. A compound according to claim 1, selected from the group consisting of:
O-ethyl-S-(2-propynyl)-(2,2,4-trimethyl-3-thiazolin-5-ylideneaminooxy)phosphonodithioate,
O-ethyl-S-(2-propenyl)-(2,2,4-trimethyl-3-thiazolin-5-ylideneaminooxy)phosphonodithioate,
O-ethyl-S-ethyl-(2,2,4-trimethyl-3-thiazolin-5-ylideneaminooxy)phosphonodithioate,
O,O-diethyl-(2,2,4-trimethyl-3-thiazolin-5-ylideneaminooxy)phosphonate,
O-ethyl-S-(n-propyl)-(2-cyclopropyl-2,4-dimethyl-3-thiazolin-5-ylideneaminooxy)phosphonothioate,
O-ethyl-S-(n-propyl)-(2-isopropyl-4-methyl-3-thiazolin-5-ylideneaminooxy)phosphonothioate,
O-ethyl-S-(n-propyl)-(2-ethyl-2,4-dimethyl-3-thiazolin-5-ylideneaminooxy)phosphonothioate,
O-ethyl-S-(n-propyl)-(2,4-dimethyl-3-thiazolin-5-ylideneaminooxy)phosphonodithioate,
O-ethyl-S-(n-propyl)-(2,4-dimethyl-3-thiazolin-5-ylideneaminooxy)phosphonothioate,
O,O-diethyl-(4,4,5-trimethyl-3-thiazolin-2-ylideneaminooxy)phosphonate,
O-ethyl-(4,4,5-trimethyl-3-thiazolin-2-ylideneaminooxy)phosphonothioate dimethylamide,
O-ethyl-S-(sec.butyl)-(4,4,5-trimethyl-3-thiazolin-2-ylideneaminooxy)phosphonodithioate,
O-ethyl-S-(2-propenyl)-(4,4,5-trimethyl-3-thiazolin-2-ylideneaminooxy)phosphonodithioate,
O,O-diethyl-(4-ethyl-4,5-dimethyl-3-thiazolin-2-ylideneaminooxy)phosphonothioate and
O,O-diethyl-(4-ethyl-4,5-dimethyl-3-thiazolin-2-ylideneaminooxy)phosphonate.

12. A pesticidal composition which comprises an inert carrier material and, as the active ingredient, an amount which is effective as a pesticide of a compound of the formula

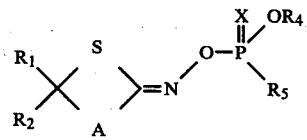  I wherein
A is a group

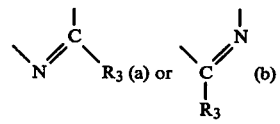

$R_1$ and $R_2$ are hydrogen, lower alkyl or cycloalkyl, or together with the carbon atom to which they are attached are a 4- to 6-membered, saturated hydrocarbon ring,
$R_3$ is lower alkyl, cycloalkyl or lower alkylthio,
X is oxygen or sulphur,
$R_4$ is lower alkyl,
$R_5$ is lower alkoxy, lower alkylthio, lower alkenylthio, lower alkynylthio, lower alkylamino or di(lower alkyl) amino, with the proviso that $R_1$, $R_2$ and $R_3$ are lower alkyl groups when A represents a group (b).

13. The pesticidal composition of claim 12 wherein the active ingredient is selected from the group consisting of
O,O-Diethyl-(2,2,4-trimethyl-3-thiazolin-5-ylideneaminooxy)phosphonothioate,
O,O-dimethyl-(2,2,4-trimethyl-3-thiazolin-5-ylideneaminooxy)phosphonothioate,
O-ethyl-S-(n-propyl)-(2,2,4-trimethyl-3-thiazolin-5-ylideneaminooxy)phosphonothioate,
O-ethyl-(2,2,4-trimethyl-3-thiazolin-5-ylideneaminooxy)phosphonothioate isopropylamide,
O-ethyl-S-(n-propyl)-(2-ethyl-2,4-dimethyl-3-thiazolin-5-ylideneaminooxy)phosphonodithioate,
O-ethyl-S-(n-propyl)-[2-ethyl-2-(n-butyl)-4-methyl-3-thiazolin-5-ylideneaminooxy]phosphonodithioate,
O-ethyl-S-(n-propyl)-(2-isopropyl-4-methyl-3-thiazolin-5-ylideneaminooxy)phosphonodithioate,
O-ethyl-S-(n-propyl)-(2-cyclcopropyl-2,4-dimethyl-3-thiazolin-5-ylideneaminooxy)phosphonodithioate,
O-ethyl-S-(n-propyl)-(2,2-tetramethylene-4-methyl-3-thiazolin-5-ylideneaminooxy)phosphonodithioate,
O-ethyl-S-(n-propyl)-(2,2-dimethyl-4-isopropyl-3-thiazolin-5-ylideneaminooxy)phosphonodithioate,
O-ethyl-S-(n-propyl)-(2,2-dimethyl-4-isopropyl-3-thiazolin-5-ylideneaminooxy)phosphonothioate,
O-ethyl-S-(n-propyl)-(2,2-dimethyl-4-methylthio-3-thiazolin-5-ylideneaminooxy)phosphonodithioate,
O-ethyl-S-(sec.butyl)-(2,2,4-trimethyl-3-thiazolin-5-ylideneaminooxy)phosphonodithioate,
O-ethyl-S-(n-propyl)-(4,5-dimethyl-5-ethyl-3-thiazolin-2-ylideneaminooxy)phosphonothioate,
O,O-diethyl-(4,4,5-trimethyl-3-thiazolin-2-ylideneaminooxy)phosphonothioate,
O-ethyl-S-(n-propyl)-(4,5,5-trimethyl-3-thiazolin-2-ylideneaminooxy)phosphonodithioate,
O-ethyl-S-(n-propyl)-(4,5,5-trimethyl-3-thiazolin-2-ylideneaminooxy)phosphonothioate and
O-ethyl-S-(n-propyl)-(4,5-dimethyl-5-ethyl-3-thiazolin-2-ylideneaminooxy)phosphonodithioate.

14. The pesticidal composition of claim 12 wherein the active ingredient is selected from the group consisting of
O-ethyl-S-(2-propynyl)-(2,2,4-trimethyl-3-thiazolin-5-ylideneaminooxy)phosphonodithioate,
O-ethyl-S-(2-propenyl)-(2,2,4-trimethyl-3-thiazolin-5-ylideneaminooxy)phosphonodithioate,
O-ethyl-S-ethyl-(2,2,4-trimethyl-3-thiazolin-5-ylideneaminooxy)phosphonodithioate,
O,O-diethyl-(2,2,4-trimethyl-3-thiazolin-5-ylideneaminooxy)phosphonate,
O-ethyl-S-(n-propyl)-(2-cyclopropyl-2,4-dimethyl-3-thiazolin-5-ylideneaminooxy)phosphonothioate,
O-ethyl-S-(n-propyl)-(2-isopropyl-4-methyl-3-thiazolin-5-ylideneaminooxy)phosphonothioate,
O-ethyl-S-(n-propyl)-(2-ethyl-2,4-dimethyl-3-thiazolin-5-ylideneaminooxy)phosphonothioate,
O-ethyl-S-(n-propyl)-(2,4-dimethyl-3-thiazolin-5-ylideneaminooxy)phosphonodithioate,
O-ethyl-S-(n-propyl)-(2,4-dimethyl-3-thiazolin-5-ylideneaminooxy)phosphonothioate,
O,O-diethyl-(4,4,5-trimethyl-3-thiazolin-2-ylideneaminooxy)phosphonate,
O-ethyl-(4,4,5-trimethyl-3-thiazolin-2-ylideneaminooxy)phosphonothioate dimethylamide, O-ethyl-S-(sec.butyl)-(4,4,5-trimethyl-3-thiazolin-2-ylideneaminooxy)phosphonodithioate,
O-ethyl-S-(2-propenyl)-(4,4,5-trimethyl-3-thiazolin-2-ylideneaminooxy)phosphonodithioate,
O,O-diethyl-(4-ethyl-4,5-dimethyl-3-thiazolin-2-ylideneaminooxy)phosphonothioate and
O,O-diethyl-(4-ethyl-4,5-dimethyl-3-thiazolin-2-ylideneaminooxy)phosphonate.

15. The pesticidal composition of claim 12 wherein the active ingredient is O-ethyl-S-(n-propyl)-(2,2,4-trimethyl-3-thiazolin-5-ylideneaminooxy)phosphonodithioate.

16. A method for the control of pests which comprises applying to the site to be treated an amount of the pesticidal composition of claim 12 which is effective in the control of pests.

17. The method of claim 16 wherein the active ingredient of the pesticidal composition is selected from the group consisting of
O,O-Diethyl-(2,2,4-trimethyl-3-thiazolin-5-ylideneaminooxy)phosphonothioate,
O,O-dimethyl-(2,2,4-trimethyl-3-thiazolin-5-ylideneaminooxy)phosphonothioate,
O-ethyl-S-(n-propyl)-(2,2,4-trimethyl-3-thiazolin-5-ylideneaminooxy)phosphonothioate,
O-ethyl-(2,2,4-trimethyl-3-thiazolin-5-ylideneaminooxy)phosphonothioate isopropylamide,
O-ethyl-S-(n-propyl)-(2-ethyl-2,4-dimethyl-3-thiazolin-5-ylideneaminooxy)phosphonodithioate,
O-ethyl-S-(n-propyl)-[2-ethyl-2-(n-butyl)-4-methyl-3-thiazolin-5-ylideneaminooxy]phosphonodithioate,
O-ethyl-S-(n-propyl)-(2-isopropyl-4-methyl-3-thiazolin-5-ylideneaminooxy)phosphonodithioate,
O-ethyl-S-(n-propyl)-(2-cylcopropyl-2,4-dimethyl-3-thiazolin-5-ylideneaminooxy)phosphonodithioate,
O-ethyl-S-(n-propyl)-(2,2-tetramethylene-4-methyl-3-thiazolin-5-ylideneaminooxy)phosphonodithioate,
O-ethyl-S-(n-propyl)-(2,2-dimethyl-4-isopropyl-3-thiazolin-5-ylideneaminooxy)phosphonodithioate,
O-ethyl-S-(n-propyl)-(2,2-dimethyl-4-isopropyl-3-thiazolin-5-ylideneaminooxy)phosphonothioate,
O-ethyl-S-(n-propyl)-(2,2-dimethyl-4-methylthio-3-thiazolin-5-ylideneaminooxy)phosphonodithioate,
O-ethyl-S-(sec.butyl)-(2,2,4-trimethyl-3-thiazolin-5-ylideneaminooxy)phosphonodithioate,
O-ethyl-S-(n-propyl)-(4,5-dimethyl-5-ethyl-3-thiazolin-2-ylideneaminooxy)phosphonothioate,
O,O-diethyl-(4,4,5-trimethyl-3-thiazolin-2-ylideneaminooxy)phosphonothioate,
O-ethyl-S-(n-propyl)-(4,5,5-trimethyl-3-thiazolin-2-ylideneaminooxy)phosphonodithioate,
O-ethyl-S-(n-propyl)-(4,5,5-trimethyl-3-thiazolin-2-ylideneaminooxy)phosphonothioate and
O-ethyl-S-(n-propyl)-(4,5-dimethyl-5-ethyl-3-thiazolin-2-ylideneaminooxy)phosphonodithioate.

18. The method of claim 16 wherein the active ingredient of the pesticidal composition is selected from the group consisting of
O-ethyl-S-(2-propynyl)-(2,2,4-trimethyl-3-thiazolin-5-ylideneaminooxy)phosphonodithioate,
O-ethyl-S-(2-propenyl)-(2,2,4-trimethyl-3-thiazolin-5-ylideneaminooxy)phosphonodithioate,
O-ethyl-S-ethyl-(2,2,4-trimethyl-3-thiazolin-5-ylideneaminooxy)phosphonodithioate,
O,O-diethyl-(2,2,4-trimethyl-3-thiazolin-5-ylideneaminooxy)phosphonate,
O-ethyl-S-(n-propyl)-(2-cyclopropyl-2,4-dimethyl-3-thiazolin-5-ylideneaminooxy)phosphonothioate,
O-ethyl-S-(n-propyl)-(2-isopropyl-4-methyl-3-thiazolin-5-ylideneaminooxy)phosphonothioate,
O-ethyl-S-(n-propyl)-(2-ethyl-2,4-dimethyl-3-thiazolin-5-ylideneaminooxy)phosphonothioate,
O-ethyl-S-(n-propyl)-(2,4-dimethyl-3-thiazolin-5-ylideneaminooxy)phosphonodithioate,
O-ethyl-S-(n-propyl)-(2,4-dimethyl-3-thiazolin-5-ylideneaminooxy)phosphonothioate,
O,O-diethyl-(4,4,5-trimethyl-3-thiazolin-2-ylideneaminooxy)phosphonate,
O-ethyl-(4,4,5-trimethyl-3-thiazolin-2-ylideneaminooxy)phosphonothioate dimethylamide,
O-ethyl-S-(sec.butyl)-(4,4,5-trimethyl-3-thiazolin-2-ylideneaminooxy)phosphonodithioate,
O-ethyl-S-(2-propenyl)-(4,4,5-trimethyl-3-thiazolin-2-ylideneaminooxy)phosphonodithioate,
O,O-diethyl-(4-ethyl-4,5-dimethyl-3-thiazolin-2-ylideneaminooxy)phosphonothioate and
O,O-diethyl-(4-ethyl-4,5-dimethyl-3-thiazolin-2-ylideneaminooxy)phosphonate.

19. The method of claim 16 wherein the active ingredient of the pesticidal composition is O-ethyl-S-(n-propyl)-(2,2,4-trimethyl-3-thiazolin-5-ylideneaminooxy) phosphonodithioate.

* * * * *